United States Patent
Monovich et al.

(10) Patent No.: US 8,586,782 B2
(45) Date of Patent: Nov. 19, 2013

(54) PHENYLACETIC ACID DERIVATIVES

(75) Inventors: Lauren G. Monovich, Belmont, MA (US); Benjamin Biro Mugrage, Cranberry, NJ (US)

(73) Assignee: Novartis AG, Basel (CH)

(*) Notice: Subject to any disclaimer, the term of this patent is extended or adjusted under 35 U.S.C. 154(b) by 0 days.

(21) Appl. No.: 13/611,365

(22) Filed: Sep. 12, 2012

(65) Prior Publication Data
US 2013/0012585 A1 Jan. 10, 2013

Related U.S. Application Data

(63) Continuation of application No. 12/305,531, filed as application No. PCT/US2007/071979 on Jun. 25, 2007, now Pat. No. 8,362,294.

(60) Provisional application No. 60/805,784, filed on Jun. 26, 2006.

(51) Int. Cl.
C07C 205/00 (2006.01)
C07C 207/00 (2006.01)

(52) U.S. Cl.
USPC .......................................................... 562/435

(58) Field of Classification Search
None
See application file for complete search history.

(56) References Cited

U.S. PATENT DOCUMENTS

| | | | |
|---|---|---|---|
| 4,410,724 A | 10/1983 | Takase et al. | |
| 5,958,978 A | 9/1999 | Yamazaki et al. | |

FOREIGN PATENT DOCUMENTS

| | | |
|---|---|---|
| GB | 1139332 | 4/1969 |
| GB | 1257190 | 12/1971 |
| JP | 51-149252 | 12/1976 |
| JP | 52-68159 | 6/1977 |
| JP | 52-83822 | 7/1977 |
| WO | 82/01366 A1 | 4/1982 |
| WO | 94/04484 A1 | 3/1994 |
| WO | 97/09977 A1 | 3/1997 |
| WO | 99/11605 A1 | 3/1999 |
| WO | 00/76969 A1 | 12/2000 |
| WO | 01/03684 A2 | 1/2001 |
| WO | 01/23346 A2 | 4/2001 |
| WO | 2004/048314 A1 | 6/2004 |

OTHER PUBLICATIONS

Sorbera et al., "Lumiracoxib" Drugs of the Future 27(8):740-747 (2002).
Nohara et al., "[o-(2,4-Dichloro-1-naphthylamino)phenyl]acetic acid" 6001 Chemical Abstracts, Columbus, Ohio, US 87(15):585 XP-002273659 (Oct. 10, 1977).
Nohara et al., "Naphthylaminophenylacetic acid derivatives," 6001 Chemical Abstracts, Columbus, Ohio US 81(1):461 XP-002273660 (Apr. 7, 1977).
Nohara et al., "(Naphthylaminophenyl)acetic acids and their salts," 6001 Chemical Abstracts, Columbus Ohio, US 88(3):596 XP-002273661 (Jan. 16, 1978).
Denny et al., "Potential Antitumor Agents. 36. Quantitative Relationships between Experimental Antitumor Activity, Toxicity, and Structure for the General Class of 9-Anilinoacridine Antitumor Agents," J. Med. Chem. 25:276-315 (1982).
Rowlinson et al., "A Novel Mechanism of Cyclooxygenase-2 Inhibition Involving Interactions with Ser-530 and Tyr-385," Journal of biological Chemistry, vol. 278, No. 46, Nov. 2003, pp. 45763-45769.
Moser et al., J. Med. Chem., 33:2358-2368 (1990).

*Primary Examiner* — Sudhakar Katakam
*Assistant Examiner* — Jennifer C Sawyer
(74) *Attorney, Agent, or Firm* — John B. Alexander

(57) ABSTRACT

Compounds of formula (I) pharmaceutically acceptable salts thereof; and pharmaceutically acceptable esters thereof; which are useful for the treatment of COX-2 dependent disorders.

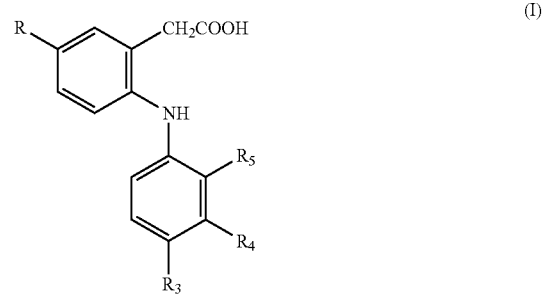

1 Claim, No Drawings

PHENYLACETIC ACID DERIVATIVES

This application is a continuation of U.S. Ser. No. 12/305,531 filed Dec. 18, 2008 which is a U.S. National Stage of PCT/US07/71979 filed Jun. 25, 2007 which claims the benefit of U.S. 60/805,784 filed Jun. 26, 2006.

The invention relates to phenylacetic acids and derivatives as defined herein which are particularly potent and selective cyclooxygenase-2 (COX-2) inhibitors, methods for preparation thereof, pharmaceutical compositions comprising said compounds, methods of selectively inhibiting COX-2 activity and of treating conditions in mammals which are responsive to COX-2 inhibition using said compounds or pharmaceutical compositions comprising said compounds of the invention.

The present invention provides novel phenylacetic acids and derivatives which inhibit COX-2 without significantly inhibiting cyclooxygenase-1 (COX-1). The invention thus provides novel non-steroidal anti-inflammatory agents which are surprisingly free of undesirable side effects usually associated with the classical non-steroidal anti-inflammatory agents, such as gastrointestinal and renal side effects.

The compounds of the present invention are thus particularly useful or may be metabolically converted to compounds which are particularly useful as selective COX-2 inhibitors. They are thus particularly useful for the treatment of COX-2 dependent disorders in mammals, including inflammation, pyresis, pain, osteoarthritis, rheumatoid arthritis, dysmenorrhea, migraine headache, cancer (such as of the digestive tract, e.g., colon cancer and melanoma), cancer pain, acute pain, chronic pain, neurodegenerative diseases (such as multiple sclerosis, Parkinson's disease and Alzheimer's disease), cardiovascular disorders (such as atherosclerosis, coronary artery disease and arteriosclerosis), osteoporosis, gout, acute gout, asthma, lupus and psoriasis while substantially eliminating undesirable gastrointestinal ulceration associated with conventional cyclooxygenase (COX) inhibitors. The compounds of the invention are also UV absorbers, in particular, UV-B absorbers, and are useful for blocking or absorbing UV radiation, for instance, for the treatment and prevention of sunburn, e.g., in suntan products.

Ocular applications of the compounds of the invention include the treatment of ocular inflammation, wet age-related macular degeneration, ocular pain including pain associated with ocular surgery, such as PRK or cataract surgery, of ocular allergy, of photophobia of various etiology, of elevated intraocular pressure (in glaucoma) by inhibiting the production of trabecular meshwork inducible glucocorticoid response protein and of dry eye disease.

The compounds of the present invention are useful for the treatment of neoplasia particularly neoplasia that produce prostaglandins or express COX, including both benign and cancerous tumors, growths and polyps, in particular, epithelium cell-derived neoplasia. Compounds of the present invention are, in particular, useful for the treatment of liver, bladder, pancreatic, ovarian, prostate, cervical, lung and breast cancer and, especially gastrointestinal cancer, e.g., cancer of the colon, and skin cancer, e.g., squamous cell or basal cell cancers and melanoma, as indicated above.

The term "treatment" as used herein is to be understood as including both therapeutic and prophylactic modes of therapy, e.g., in relation to the treatment of neoplasia, therapy to prevent the onset of clinically or pre-clinically evident neoplasia, or for the prevention of initiation of malignant cells or to arrest or reverse the progression of pre-malignant to malignant cells, as well as the prevention or inhibition of neoplasia growth or metastasis. In this context, the present invention is, in particular, to be understood as embracing the use of compounds of the present invention to inhibit or prevent development of skin cancer, e.g., squamous or basal cell carcinoma consequential to UV light exposure, e.g., resulting from chronic exposure to the sun. The compounds may be used in humans or in other mammals.

In a first aspect of the invention there is provided a compound of formula

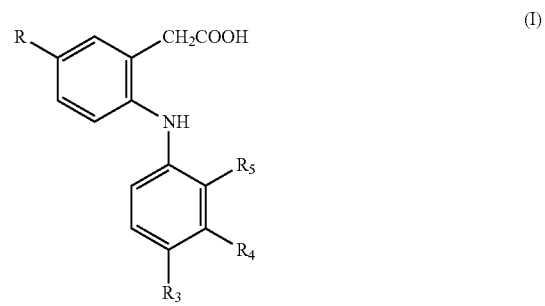

wherein
R is methyl or ethyl;
$R_3$ is halo or $C_1$-$C_6$ alkyl;
$R_4$ is $C_1$-$C_6$ alkyl;
$R_5$ is halo;
the above mentioned $C_1$-$C_6$ alkyl at $R_3$ and $R_4$ being optionally substituted by one or more halo groups;
pharmaceutically acceptable salts thereof; and pharmaceutically acceptable esters thereof.

Preferably in compounds of formula (I), $R_3$ is halo, methyl or ethyl. More preferably it is halo. Alternatively preferably it is chloro.

Preferably in compounds of formula (I), $R_4$ is $C_1$-$C_3$ alkyl, optionally substituted by one or more halo groups. More preferably it is methyl, ethyl, isopropyl or trifluoromethyl. Yet more preferably it is methyl. Alternatively preferably it is trifluoromethyl.

Preferably in compounds of formula (I), $R_5$ is chloro or fluoro.

Yet more preferably both $R_3$ and $R_5$ are independently selected from chloro and fluoro.

Preferably the compound is selected from the following list of compounds:
5-methyl-2-(2',4'-dichloro-3'-methylanilino)phenylacetic acid
5-ethyl-2-(2',4'-dichloro-3'-methylanilino)phenylacetic acid
5-methyl-2-(2'-fluoro-3'-trifluoromethyl-4'-ethylanilino) phenylacetic acid
5-ethyl-2-(2'-fluoro-3'-trifluoromethyl-4'-ethylanilino)phenylacetic add
5-methyl-2-(2'-fluoro-3'-trifluoromethyl-4'-methylanilino) phenylacetic acid
5-ethyl-2-(2'-fluoro-3'-trifluoromethyl-4'-methylanilino) phenylacetic acid
5-methyl-2-(2'-fluoro-3'-methyl-4'chloroanilino)phenylacetic acid
5-ethyl-2-(2'-fluoro-3'-methyl-4'chloroanilino)phenylacetic acid
5-methyl-2-(2'-fluoro-3'-ethyl-4'chloroanilino)phenylacetic acid
5-ethyl-2-(2'-fluoro-3'-ethyl-4'chloroanilino)phenylacetic acid
5-methyl-2-(2',4'-dichloro-3'-ethylanilino)phenylacetic acid
5-ethyl-2-(2',4'-dichloro-3'-ethylanilino)phenylacetic acid 5-ethyl-2-(2'-fluoro-3'-isopropyl-4'chloroanilino)phenylacetic acid
5-Methyl-2-(2',4'-dichloro-3'-methylanilino)phenylacetic acid diethylamine salt
sodium 5-Methyl-2-(2',4'-dichloro-3'-methylanilino)phenylacetate
5-Methyl-2-(2',4'-dichloro-3'-methylanilino)phenylacetic acid tromethamine salt
calcium 5-Methyl-2-(2',4'-dichloro-3'-methylanilino)phenylacetate monohydrate
Lysine 5-Methyl-2-(2',4'-dichloro-3'-methylanilino)phenylacetate monohydrate
choline 5-Methyl-2-(2',4'-dichloro-3'-methylanilino)phenylacetate monohydrate
Potassium 5-Methyl-2-(2',4'-dichloro-3'-methylanilino)phenylacetate.

In a second aspect, the invention provides a pharmaceutical composition comprising an effective amount of a compound of formula (I) in combination with one or more pharmaceutically acceptable carriers.

In a third aspect, the invention provides a method of treating cyclooxygenase-2 (COX-2) dependent disorders in mammals which comprises administering to a mammal in need thereof an effective amount of a compound of formula (I).

In a fourth aspect, the invention provides a method of selectively inhibiting COX-2 activity in a mammal without substantially inhibiting cyclooxygenase-1 activity which comprises administering to a mammal in need thereof an effective COX-2 inhibiting amount of a compound of formula (I).

In a fifth aspect, the invention provides a method of treating rheumatoid arthritis, osteoarthritis, dysmenorrhea, pain, tumors or inflammation in mammals which comprises administering to a mammal in need thereof a correspondingly effective amount of a compound of formula (I).

In a sixth aspect, the invention provides the use of a compound of formula (I) in the manufacture of a medicament for the treatment of rheumatoid arthritis, osteoarthritis, dysmenorrhea, pain, tumors or inflammation.

In a seventh aspect, the invention provides a compound of formula (I) for use in the treatment of a COX-2 dependent disorder.

In an eighth aspect, the invention provides a method for the preparation of a compound of formula (I) of claim 1 which comprises the step of:

(a) coupling a compound of formula (II) or (III)

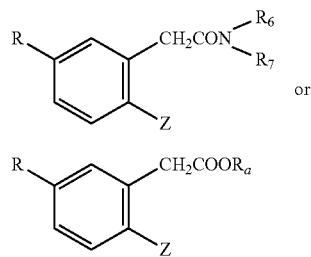

wherein
Z is bromo or iodo;
R has meaning as defined above;
$R_a$ is hydrogen, an alkali metal cation or lower alkyl, preferably isopropyl; and $R_6$ and $R_7$ are lower alkyl; or $R_6$ and $R_7$, together with the nitrogen atom, represent morpholino, piperidino or pyrrolidino;
with a compound of formula (IV)

wherein $R_3$-$R_5$ have meaning as defined above in the presence of copper and cuprous iodide to obtain a compound of formula (V) or (VI)

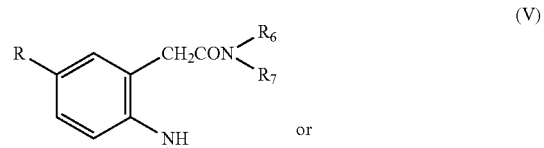

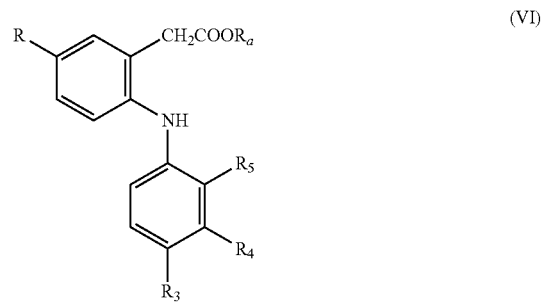

and hydrolyzing the resulting compound of formula (V) or (VI) to a compound of formula (I); or (b) condensing a compound of formula (VII)

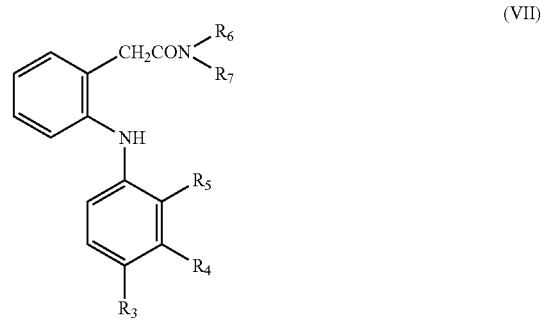

wherein $R_3$-$R_7$ have meaning as defined herein, with a reactive functional derivative of an acid, e.g., acetic acid, such as acetyl chloride, in a Friedel-Crafts acylation to reaction to obtain, e.g., a compound of the formula (VIII)

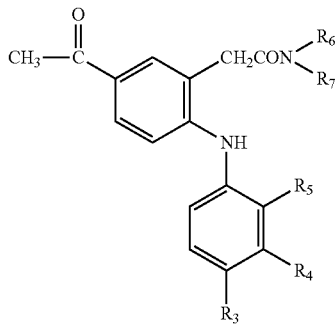

(VIII)

wherein $R_3$-$R_7$ have meaning as defined herein, which is in turn hydrogenolyzed and then hydrolyzed to obtain a compound of formula (I), wherein R represents, e.g., ethyl; or (c) hydrolyzing a lactam of formula (IX)

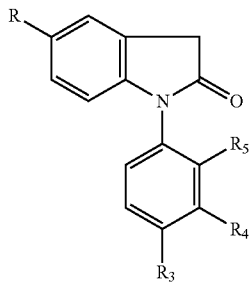

(IX)

wherein R and $R_3$-$R_5$ have meaning as defined herein, with a strong base; and in above processes, if desired, temporarily protecting any interfering reactive groups and then isolating the resulting compound of the invention; and, if desired, converting any resulting compound into another compound of the invention; and/or if desired converting a free carboxylic acid of the invention into a pharmaceutically acceptable ester derivative thereof; and/or if desired, converting a resulting free acid into a salt or a resulting salt into the free acid or into another salt.

In starting compounds and intermediates, which are converted to the compounds of the invention in a manner described herein, functional groups present, such as amino, hydroxy and carboxyl groups, are optionally protected by conventional protecting groups that are common in preparative organic chemistry. Protected hydroxy, amino and carboxyl groups are those that can be converted under mild conditions into free amino, hydroxy and carboxyl groups without other undesirable side reactions taking place. For example, hydroxy protecting groups are preferably benzyl or substituted benzyl groups, or acyl groups, such as pivaloyl.

The preparation of compounds of formulae (V) and (VI) according to process (a) is carried out under conditions of a modified Ullmann condensation for the preparation of diarylamines, e.g., in the presence of copper powder and copper (I) iodide and potassium carbonate, optionally in an inert high boiling solvent, such as nitrobenzene, toluene, xylene or N-methylpyrrolidone, at elevated temperature, e.g., in the range of 100-200° C., preferably at reflux temperature, according to general methodology described by Nohara, *Chem Abstr, Vol.* 94, p. 15402x (1951); and Moser et al., *J Med Chem, Vol.* 33, p. 2358 (1990). When Z is bromo, the condensation is carried out in the presence of an iodide salt, e.g., potassium iodide.

Hydrolysis of the resulting ortho-anilinophenylacetamides of formula (V) is carried out in aqueous alkali hydroxide, e.g., in 6 N NaOH in the presence of an alcohol, e.g., ethanol, propanol and butanol, at elevated temperature, such as reflux temperature of the reaction mixture.

The hydrolysis of esters of formula (VI) is carried out according to methods known in the art, e.g., under basic conditions as described above for the compounds of formula (V) or alternatively under acidic conditions, e.g., using methanesulfonic acid.

The starting materials of formula (II) or (III) are generally known or can be prepared using methodology known in the art, e.g. as described by Nohara in Japanese patent application No. 78/96,434 (1978); U.S. Pat. No. 6,291,523 and as illustrated herein.

For example, the corresponding anthranilic acid is converted to the ortho-diazonium derivative followed by treatment with an alkali metal iodide in acid, e.g., sulfuric acid, to obtain the 2-iodobenzoic acid or lower alkyl ester thereof. Reduction to the corresponding benzyl alcohol, e.g., with diborane or lithium aluminum hydride for the ester, conversion of the alcohol first to the bromide and then to the nitrile, hydrolysis of the nitrile to the acetic acid and conversion to the N,N-dialkylamide according to methodology known in the art yields a starting material of formula (II).

Alternatively, e.g., the starting material of formula (II), wherein Z is Br and R is cyclopropyl can be prepared by first condensing according to the method outlined in *J Am Chem Soc, Vol.* 123, p. 4155 (2001), e.g., 2-bromo-5-iodobenzoic acid methyl ester with cyclopropyl bromide in the presence of indium trichloride to obtain 2-bromo-5-cyclopropylbenzoic acid methyl ester which is converted as described above to the corresponding 2-bromo-5-cyclopropylphenylacetamide of formula (II).

Furthermore, the starting materials of formula (II), wherein R is, e.g., ethyl, can be prepared by Friedel-Crafts acetylation of oxindole with, e.g., acetyl chloride in the presence of aluminum chloride, reduction of the resulting ketone by, e.g., catalytic hydrogenolysis, followed by hydrolytic cleavage of the resulting 5-ethyloxindole to the ortho amino-phenylacetic acid. Diazotization in the presence of, e.g., potassium iodide yields the ortho iodo-phenylacetic acid which is converted to an amide of formula (II).

Esters of formula (III) are prepared from the corresponding acids according to esterification methods known in the art.

The anilines of formula (IV) are either known in the art or are prepared according to methods well-known in the art, and as illustrated herein.

The preparation of, e.g., 5-ethyl or 5-n-propyl substituted compounds according to process (b) is carried out under conditions of Friedel-Crafts acylation, e.g., in the presence of aluminum chloride in an inert solvent, such as 1,2-dichloroethane, followed by hydrogenolysis, e.g., using palladium on charcoal catalyst, preferably in acetic acid as solvent, at room temperature and about 3 atmospheres pressure.

The starting materials of formula (VII) are prepared generally as described under process (a) starting with an amide of formula (II) in which R represents hydrogen, e.g., as described in Moser et al. (1990), supra.

The preparation of the compounds of the invention according to process (c) can be carried out under conditions known in the art for the hydrolytic cleavage of lactams, preferably with a strong aqueous base, such as aqueous sodium hydroxide, optionally in the presence of an organic water miscible solvent, such as methanol at elevated temperature in the range of about 50-100° C., as generally described in U.S. Pat. No. 3,558,690.

The oxindole starting materials of formula (IX) are prepared by N-acylation of a diarylamine of the formula (X)

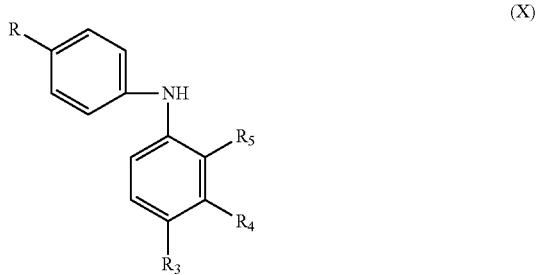

(X)

wherein R and $R_1$-$R_5$ have meaning as defined above, with a haloacetyl chloride, preferably chloroacetyl chloride, advantageously at elevated temperature, e.g., near 100° C., to obtain a compound of the formula (XI)

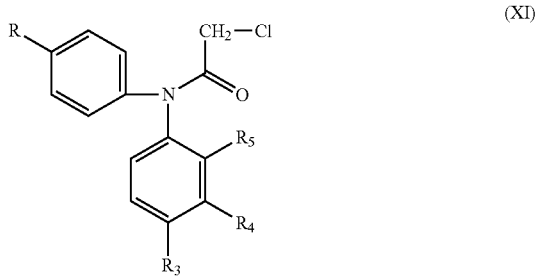

(XI)

wherein R and $R_3$-$R_5$ have meaning as defined hereinabove. Cyclization of a compound of formula (XI) is carried out under conditions of Friedel-Crafts alkylation in an inert solvent, such as dichlorobenzene, in the presence of Friedel-Crafts catalysts, e.g., aluminum chloride and ethylaluminum dichloride, at elevated temperature, e.g., at 120-175° C.

The starting amines of formula (X) can be prepared by an Ullmann condensation and other methods known in the art, e.g., a Buchwald coupling reaction.

Esters of the carboxylic acids of formula (I) are prepared by condensation of the carboxylic acid, in the form of a salt or in the presence of a base, with a halide (bromide or chloride) corresponding to the esterifying alcohol, such as benzyl chloroacetate, according to methodology well-known in the art, e.g., in a polar solvent, such as N,N-dimethylformamide, and if required further modifying the resulting product. For example, if the esterification product is itself an ester, such can be converted to the carboxylic acid, e.g., by hydrogenolysis of a resulting benzyl ester. Also if the esterification product is itself a halide, such can for instance be converted to the nitrooxy derivative by reaction with, e.g., silver nitrate.

For example, the compounds of formula (Ia) are preferably prepared by condensing a salt of a carboxylic acid of formula (I) above with a compound of formula $$X—CH_2—COOR_b$$

wherein
X is a leaving group; and
$R_b$ is a carboxy-protecting group;
to obtain a compound of formula (Ia) in carboxy-protected form, and subsequently removing the protecting group $R_b$.

The esterification can be carried under esterification conditions known in the art, e.g., in a polar solvent, such as N,N-dimethylformamide, at a temperature range of room temperature to about 100° C., preferably at a range of 40-60° C., e.g., according to the procedure described in U.S. Pat. No. 5,291,523.

The salt of the acid of formula (I) is preferably an alkali metal salt, e.g., the sodium salt which may be prepared in situ.

Leaving group X is preferably halo, e.g., chloro or bromo, or lower alkylsulfonyloxy, e.g., methanesulfonyloxy.

Carboxy-protecting group $R_b$ is preferably benzyl.

The resulting benzyl esters can be converted to the free acids of formula (Ia) preferably by hydrogenolysis with hydrogen in the presence of, e.g., Pd/C catalyst in acetic acid at atmospheric pressure or under Parr hydrogenation at a temperature ranging from room temperature to about 50° C.

The invention includes any novel starting materials and processes for their manufacture.

Finally, compounds of the invention are either obtained in the free form, or as a salt thereof if salt forming groups are present.

The acidic compounds of the invention may be converted into metal salts with pharmaceutically acceptable bases, e.g., an aqueous alkali metal hydroxide, advantageously in the presence of an ethereal or alcoholic solvent, such as a lower alkanol. Resulting salts may be converted into the free compounds by treatment with acids. These or other salts can also be used for purification of the compounds obtained. Ammonium salts are obtained by reaction with the appropriate amine, e.g., diethylamine, and the like.

Compounds of the invention having basic groups can be converted into acid addition salts, especially pharmaceutically acceptable salts. These are formed, e.g., with inorganic acids, such as mineral acids, e.g., sulfuric acid, a phosphoric or hydrohalic acid; or with organic carboxylic acids, such as ($C_1$-$C_4$)alkanecarboxylic acids which, e.g., are unsubstituted or substituted by halogen, e.g., acetic acid, such as saturated or unsaturated dicarboxylic acids, e.g., oxalic, succinic, maleic or fumaric acid, such as hydroxycarboxylic acids, e.g., glycolic, lactic, malic, tartaric or citric acid, such as amino acids, e.g., aspartic or glutamic acid; or with organic sulfonic acids, such as ($C_1$-$C_4$)alkylsulfonic acids, e.g., methanesulfonic acid; or arylsulfonic acids which are unsubstituted or substituted, e.g., by halogen. Preferred are salts formed with hydrochloric acid, methanesulfonic acid and maleic acid.

In view of the close relationship between the free compounds and the compounds in the form of their salts, whenever a compound is referred to in this context, a corresponding salt is also intended, provided such is possible or appropriate under the circumstances.

The compounds, including their salts, can also be obtained in the form of their hydrates, or include other solvents used for their crystallization.

The general definitions used herein have the following meaning within the scope of the present invention, unless otherwise indicated.

Pharmaceutically acceptable esters are preferably prodrug ester derivatives which are convertible by solvolysis or under physiological conditions to the free carboxylic acids of, e.g., formula (I). Such esters are, e.g., lower alkyl esters, such as the methyl or ethyl ester; carboxy-lower alkyl esters, such as the carboxymethyl ester; nitrooxy- or nitrosooxy-lower alkyl esters, such as the 4-nitrooxybutyl or 4-nitrosooxybutyl ester; and the like. Preferred are the phenylacetoxyacetic acids of formula (Ia)

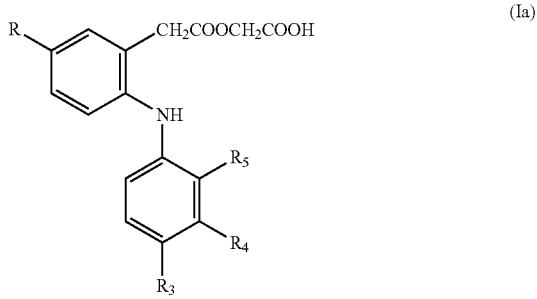

wherein R, $R_3$, $R_4$ and $R_5$ have meaning as defined hereinabove for compounds of formula (I); and pharmaceutically acceptable salts thereof.

Pharmaceutically acceptable salts represent metal salts, such as alkaline metal salts, e.g., sodium, potassium, magnesium or calcium salts; as well as ammonium salts, which are formed, e.g., with ammonia and mono- or di-alkylamines, such as diethylammonium salts; and with amino acids, such as arginine and histidine salts.

A lower alkyl group contains up to 6 carbon atoms, preferably 1-4 carbon atoms, may be straight chain or branched and represents, e.g., methyl, ethyl, propyl, butyl, isopropyl, isobutyl and the like, preferably methyl or ethyl. Lower alkoxy is methoxy, ethoxy and the like.

Halo is preferably chloro, bromo or fluoro, advantageously chloro or fluoro.

The compounds of the invention are useful as selective COX-2 inhibitors or as prodrugs thereof. The selective COX-2 inhibitors and prodrugs thereof of the invention are particularly useful for the treatment of, e.g., inflammation, pyresis, pain, osteoarthritis, dysmenorrhea, rheumatoid arthritis and other conditions responsive to the inhibition of COX-2 and are typically substantially free of undesirable gastrointestinal side effects associated with conventional non-steroidal anti-inflammatory agents.

The above-cited properties are demonstrable in vitro and in vivo tests using advantageously mammals, e.g., rats, mice, dogs, monkeys and isolated cells or enzyme preparations of human and non-human origin. Said compounds can be applied in vitro in the form of solutions, e.g., aqueous solutions, and in vivo advantageously orally, topically or parenterally, e.g., intravenously. The dosage in vitro may range from about $10^{-5}$-$10^{-9}$ molar concentrations. The dosage in vivo may range, depending on the route of administration, between about 0.1 mg/kg and 100 mg/kg.

The biological properties can be demonstrated in tests well-known in the art, e.g., as described in U.S. Pat. No. 6,291,523, and as described herein.

COX-2 inhibition is determined in an enzymatic in vitro assay using a commercially available kit (Cayman Chemical Company).

The test compound (stock solution in DMSO diluted with buffer to various concentrations) is pre-incubated with 30-50 units of purified recombinant human COX-2 and hematin (1 µM) for 30 minutes at 25° C., followed by incubation with 100 µM arachidonic acid and the colorimetric substrate TMPD (N,N,N',N'-tetramethyl-p-phenylenediamine) for 5-7 minutes at 25° C., followed by colorimetric detection of oxidized TMPD at 590 nm. The COX-2 activity in the presence of test compound is compared to COX-2 activity for control without test compound.

COX inhibition is also determined in vitro using cellular assays for inhibition of both COX-1 and COX-2.

Cellular assays for testing COX inhibitors are well-known in the art and based on the fact that the COX enzyme (prostaglandin H synthase) catalyzes the rate limiting step in prostaglandin synthesis from arachidonic acid. Two enzymes mediate the reaction: COX-1 is a constitutive form of the enzyme whereas COX-2 is induced in response to various growth factors and cytokines.

In vitro COX-1 and COX-2 inhibition is determined in the cell-based assays in order to assess the in vitro activity and selectivity for COX-2 inhibition, using a prostaglandin $E_2$ immunoassay (Cayman $PGE_2$ Kit). The cells utilized are HEK-293 EBNA cells that have been transfected and have a stable expression of either recombinant human COX-1 or recombinant human COX-2, respectively. Cells are plated out into 96-well plates in which the assay is performed. Both cell lines are pre-treated with compound dilutions for 30 minutes at 37° C., then arachidonic acid (1 µM) is added as exogenous substrate. The supernatant is harvested 15 minutes later and the production of $PGE_2$ is measured by immunoassay. For $IC_{50}$ determinations, compounds are tested at 5-9 concentrations in singlet, duplicate or quadruplicate replicates at each concentration (highest concentration 30 µM). The mean inhibition of $PGE_2$ (compared to cells not treated with compound) for each concentration is calculated, a plot is made of mean % inhibition versus log compound concentration, and the $IC_{50}$ value calculated using a 4-parameter logistic fit. The relative effects on each enzyme are compared to assess selectivity for inhibition of COX-2.

In vitro COX-1 and COX-2 inhibition is also determined in human whole blood where COX-1 is constitutively expressed in platelets and COX-2 expression is induced in mononuclear cells by treatment with lipopolysaccharide (LPS) (10 µg/mL). For this assay heparinized human blood is divided into two aliquots: one for measuring $TxB_2$ production (a surrogate indicator of COX-1 activity) and a second for measuring $PGE_2$ production (a surrogate for COX-2 activity). The blood samples are pretreated with test compounds for one hour before stimulation. Compounds are tested in a final concentration range from 0.1 nM to 300 µM using half log increases in concentrations. To measure inhibition of thromboxane $B_2$ ($TxB_2$) generation, A23187 (50 µM) is added, and the blood incubated for one hour. $PGE_2$ production is measured after the addition of LPS (10 µg/mL) followed by overnight incubation. After incubation with A23187 or LPS the samples are centrifuged at 250×g for 10 minutes at 4° C. to collect serum. The amounts $PGE_2$ and $TxB_2$ present in the serum are measured using a chemiluminesence enzyme immunoassay from Assay Designs Inc. (Ann Arbor, Mich.). The levels of prostaglandin in each sample are normalized to the percent inhibition caused by each concentration of the test compound. The percent inhibition data for each donor is pooled and fitted to a 4-parameter logistic function using a regression.

$IC_{50}$ values for compounds of formula (I) in the COX-2 inhibition assays are as low as about 0.10 µM or even lower. Preferred are compounds for which the ratio of $IC_{50}$ values for COX-1 and COX-2 inhibition is above 50, advantageously in the range of about 100-1000 or higher. For example, the following $IC_{50}$ values were observed based on the above described assay, average values being taken where more than one assay was performed:

| Example | COX-2_Blood IC50 [μM] (Avg) | COX-1_Blood IC50 [μM] (Avg) |
|---|---|---|
| 5a | 0.1 | 155 |
| 5e | 0.073 | 126 |
| 5i | 0.295 | 129 |
| 5k | 0.165 | 183 |
| 5m | 0.17 | 127 |

The inhibition of prostaglandin-$E_2$ production produced by COX-2 is determined in vivo in the lipopolysaccharide (LPS)-challenged subcutaneous air pouch model in the rat. See *Advances in Inflammation Research*, Raven Press (1986); *J. Med. Chem.*, Vol. 39, p. 1846 (1996); *J. Pathol.*, Vol. 141, pp. 483-495; and *J. Pathol.*, Vol. 134, pp. 147-156.

Female Lewis rats are anesthetized and then dorsal air pouches are prepared by subcutaneous injection of 10 mL of air through a sterile 0.45 micron syringe-adapted filter. Six or 7 days after preparation, the air pouches are injected with LPS (5 μg per pouch) suspended in sterile phosphate buffered saline. Compounds for evaluation are administered by gavage one hour prior to or two or more hours after LPS challenge. The pouch contents are harvested five hours after LPS challenge and $PGE_2$ levels present in the pouch fluids are measured by enzyme immunoassay. Illustrative of the invention, the compound of Example 4(j) inhibits $PGE_2$ formation by about 50% at 1 mg/kg p.o.

Anti-inflammatory activity is determined using the carrageenan-induced rat paw edema assay following a modification of the procedure of Offerness et al., described in: *Nonsteroidal Antiinflammatory Drugs*, Lombardino, Ed., John Wiley & Sons, pp. 116-128 (1986).

Sprague Dawley rats (200-225 g) are fasted overnight, then orally dosed with the compound dissolved in 0.5% methylcellulose. After one hour, a 0.1 mL volume of 1% carrageenan in saline is injected into the sub-plantar region of the left hind paw which causes an inflammatory response. At three hours post-carrageenan, the rats are euthanized and both hind paws are cut off at the paw hair line and weighed on an electronic balance. The amount of edema in the inflamed paw is determined by subtracting the weight of the non-inflamed paw (right) from the weight of the inflamed paw (left). The percent inhibition by the compound is determined for each animal as the percent paw weight gained as compared to the control average.

The gastric tolerability assay is used to assess gross ulceration in the rat, measured four hours after oral administration of the test compound. The test is carried out as follows:

Male Sprague Dawley rats are fasted overnight, administered compound in 0.5% methylcellulose vehicle by gavage and sacrificed by carbon dioxide inhalation four hours later. The stomachs are removed and gross gastric lesions counted and measured to give the total lesion length per rat. Each experiment contains the following groups (5-6 rats per group): vehicle control, test compounds and diclofenac as a reference compound.

Data are calculated as the mean number of ulcers in a group, the mean length of ulcers (mm) in the group and as the ulcer index (UI).

UI=mean length of ulcers in a group×ulcer incidence where ulcer incidence is the fraction of animals in the group with lesions (100% incidence is 1).

Illustrative of the invention, the compounds of the Examples are essentially free of any gastric ulcerogenic effect at 30 mg/kg p.o.

Intestinal tolerability can be determined by measuring the effect on intestinal permeability. Lack of increase in permeability is indicative of intestinal tolerability.

The method used is a modification of a procedure by Davies et al., *Pharm. Res.*, Vol. 11, pp. 1652-1656 (1994) and is based on the fact that excretion of orally administered $^{51}$Cr-EDTA, a marker of small intestinal permeability, is increased by NSAIDs. Groups of male Sprague Dawley rats (≥12 per group) are administered a single, oral dose of test compound or vehicle by gastric intubation. Immediately following compound dose, each rat is administered $^{51}$Cr-EDTA (5 μCi per rat) by gastric intubation. The rats are placed in individual metabolic cages and given food and water ad libitum. Urine is collected over a 24-hour period. Twenty-four hours after administration of $^{51}$Cr-EDTA the rats are sacrificed. To quantify compound effect on intestinal permeability, the excreted $^{51}$Cr-EDTA measured in the urine of compound-treated rats is compared to the excreted $^{51}$Cr-EDTA measured in the urine of vehicle-treated rats. Relative permeability is determined by calculating the activity present in each urine sample as a percent of the administered dose after correcting for background radiation.

The analgesic activity of the compounds of the invention is determined using the complete Freund's adjuvant (CFA)-induced hyperalgesia as measured in the rat. Fifty μl of CFA is injected into the left hind paw. Nociceptive thresholds are determined prior to 24 hrs following CFA injection using standard paw-pressure apparatus (Analgesymeter, Ugo Basile, Milan). The end point is taken as paw withdrawal or struggling. Compounds are dissolved in 0.5% methylcellulose and administered orally, and further nociceptive threshold measurements are made at 1, 3 and 6 h following drug administration. In each experiment groups of 6 animals received either vehicle or one dose of compound. The results are calculated as percentage reversal of predose hyperalgesia. The dose at which 30% inhibition of the predose hyperalgesia is achieved (D30) for each compound is calculated to give an overall estimate of potency.

The anti-arthritic effect of the compounds of the invention can be determined in the well-known chronic adjuvant arthritis test in the rat.

Ocular effects can be demonstrated in well-known ophthalmic assay methods. Similarly anti-tumor activity can be demonstrated in well-known anti-tumor animal tests.

The pharmaceutical compositions according to the invention are those suitable for enteral, such as oral or rectal, transdermal, topical and parenteral administration to mammals, including man, to inhibit COX-2-activity, and for the treatment of COX-2 dependent disorders, and comprise an effective amount of a pharmacologically active compound of the invention, either alone or in combination with other therapeutic agents, and one or more pharmaceutically acceptable carriers.

More particularly, the pharmaceutical compositions comprise an effective COX-2 inhibiting amount of a selective COX-2 inhibiting compound of the invention which is substantially free of COX-1 inhibiting activity and of side effects attributed thereto.

The pharmacologically active compounds of the invention are useful in the manufacture of pharmaceutical compositions comprising an effective amount thereof in conjunction or admixture with excipients or carriers suitable for either enteral or parenteral application. Preferred are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also
c) binders, e.g., magnesium aluminum silicate, starch paste, gelatin, tragacanth, methylcellulose, sodium carboxymethylcellulose and/or polyvinylpyrrolidone; if desired
d) disintegrants, e.g., starches, agar, alginic acid or its sodium salt, or effervescent mixtures; and/or
e) absorbents, colorants, flavors and sweeteners.

Injectable compositions are preferably aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, preferably about 1-50%, of the active ingredient.

Tablets may be either film coated or enteric coated according to methods known in the art.

Suitable formulations for transdermal application include an effective amount of a compound of the invention with carrier. Advantageous carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable formulations for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application, e.g., for the treatment of skin cancer, e.g., for prophylactic use in sun creams, lotions, sprays and the like. In this regard it is noted that compounds of the present invention are capable of absorbing UV rays in the range of 290-320 nm while allowing passage of tanning rays at higher wavelengths. They are thus particularly suited for use in topical, including cosmetic, formulations well-known in the art. Such may contain solubilizers, stabilizers, tonicity enhancing agents, buffers and preservatives. Formulations suitable for topical application can be prepared, e.g., as described in U.S. Pat. No. 4,784,808. Formulations for ocular administration can be prepared, e.g., as described in U.S. Pat. Nos. 4,829,088 and 4,960,799.

The compounds of the invention may be used alone or in conjunction with other therapeutic agents. For example, suitable additional active agents for use in relation to the treatment of neoplasia (malignant and benign) include, e.g., the anti-neoplastic agents or radioprotective agents recited in International Patent Application WO 98/16227 and the like. Other suitable additional therapeutic agents include analgesic agents, such as NSAIDs, oxycodone, codeine, paracetamol, ibuprofen, tramadol, levorphanol, propoxyphene, ketorolac, pentazocine, meperidine and the like; muscle relaxants, e.g. benzothiadiazoles e.g. Sirdalud®; also anti-platelet agents, such as aspirin, clopidogrel, ticlopidine and the like; also bisphosphonates, such as zoledronate, pamidronate, risedronate, alendronate and the like; also statins, such as fluvastatin, atorvastatin, lovastatin, simvastatin, rosuvastatin, pitavastatin, pravastatin and the like; also antacids; proton pump inhibitors e.g. omeprazole, esomeprazole; calcilytics; calcitonin, e.g. oral calcitonin; an anti-IL-1 beta IgG1/kappa antibody; antihypertensives, e.g. ACE inhibitors, angiotensin II blockers, renin inhibitors.

In conjunction with another active ingredient, a compound of the invention may be administered either simultaneously, before or after the other active ingredient, either separately by the same or different route of administration or together in the same pharmaceutical formulation.

The dosage of active compound administered is dependent on the species of warm-blooded animal (mammal), the body weight, age and individual condition, and on the form of administration. A unit dosage for oral administration to a mammal of about 50-70 kg may contain between about 5 mg and 500 mg, of the active ingredient.

The present invention also relates to methods of using the compounds of the invention and their pharmaceutically acceptable salts, or pharmaceutical compositions thereof, in mammals for inhibiting COX-2 and for the treatment of conditions as described herein, e.g., inflammation, pain, rheumatoid arthritis, osteoarthritis, dysmenorrheal, tumors and other COX-2-dependent disorders.

Particularly, the present invention relates to a method of selectively inhibiting COX-2 activity in a mammal without substantially inhibiting COX-1 activity, which comprises administering to a mammal in need thereof an effective COX-2 inhibiting amount of a compound of the invention.

Thus, the present invention also relates to a method of treating COX-2 dependent disorders in mammals, which comprises administering to a mammal in need thereof an effective COX-2 inhibiting amount of a compound of the invention.

More particularly, the present invention relates to a method of treating COX-2 dependent disorders in mammals while substantially eliminating undesirable side effects associated with COX-1 inhibiting activity which comprises administering to a mammal in need thereof an effective COX-2 inhibiting amount of a selective COX-2 inhibiting compound of the invention which is substantially free of COX-1 inhibiting activity.

More specifically, such relates to a method of, e.g., treating rheumatoid arthritis, osteoarthritis, pain, dysmenorrheal, gout or inflammation in mammals without causing undesirable gastrointestinal ulceration, which method comprises administering to a mammal in need thereof a correspondingly effective amount of a compound of the invention.

The following examples are intended to illustrate the invention and are not to be construed as being limitations thereon. Temperatures are given in degrees Celsius. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR and NMR. Abbreviations and tradenames used are those conventional in the art. Typical are those given below BOC: t-butoxycarbonyl
COD: cyclooctadiene
DMAP: 4-dimethylamino-pyridine
DME: 1,2-Dimethoxyethane
DSC: differential scanning calorimetry
DMF: N,N-dimethylformamide
dppp: diphenylphospinopropane
EDCl    1-(3-dimethylaminopropyl)-3-ethylcarbodiimide hydrochloride
HOAt: 1-hydroxy-7-azabenzotriazole LAH: lithium aluminum hydride
NMM: N-methylmorpholine
Selectfluor™: 1-(chloromethyl)-4-fluoro-1,4-diazoniabicyclo[2.2.2]octane bis(tetrafluoroborate)
THF: tetrahydrofuran
TLC: thin layer chromatography

EXAMPLES

Example 1

Aniline Starting Materials

A. 2,4-Dichloro-3-methylaniline 2,4-Dichloro-3-methylaniline is prepared by reduction of 2,4-dichloro-3-methylnitrobenzene according to the procedure outlined in *Tetrahedron*, Vol. 53, No. 17, p. 6145 (1997).

B. 2,4-Dichloro-3-ethylaniline

To a solution of 2,4-dichloroaniline (42.0 g, 260 mmol) in AcOH (40.0 mL) is added $Ac_2O$ (80 mL). The reaction mixture is warmed up to 50° C. and stirred at this temperature for 1 hour. The reaction is cooled to room temperature and poured into ice water (500 mL). A solid precipitated and the mixture is stirred for additional 1 hour at room temperature. The solid is filtered and washed with water, hexanes and air dried to give N-(2,4-dichlorophenyl)acetamide.

To a solution of N-(4-chloro-2-fluorophenyl)acetamide (30.0 g, 147 mmol) in THF (300 mL) at −70° C. is added dropwise (keeping the reaction temperature below −60° C.) n-BuLi (2.0 M in cyclohexane, 147 mL, 294 mmol). The reaction is stirred between −60 to −70° C. for 2 hours and 1,1,1-trifluoro-2-iodoethane (46.2 g, 220 mmol) is added dropwise at −70° C. The reaction mixture is stirred at this temperature for additional 1.5 hours before 3N HCl (108 mL) solution is added slowly. The mixture is allowed to warm up to room temperature and extracted with EtOAc (200 mL×3). The organic layers are combined washed with water, brine and then dried over $MgSO_4$. The solvents are removed and the residue is stirred in ether and hexanes (1:2, 120 mL) for 1 hour. A solid precipitate is filtered to give N-(2,4-dichloro-3-iodophenyl)acetamide.

To a solution of N-(2,4-dichloro-3-iodophenyl)acetamide (40.0 g, 121 mmol) in MeOH (100 mL) is added concentrated HCl (50 mL). The mixture is stirred and heated at reflux for 18 hours. The mixture is cooled and the solvents were removed under reduced pressure (water bath below 45° C.). The residue is cooled with an ice bath and 3N NaOH solution was added to adjust the pH to between 9 and 10. The mixture is extracted with ether and dried over $MgSO_4$. The solvents were removed and the residue is purified through a flash chromatographic column with a gradient of hexanes/ether to give 2,4-dichloro-3-iodoaniline.

To a solution of 2,4-dichloro-3-iodoaniline (9.0 g, 31 mmol) in DME/water (180 mL/60 mL) is added vinyl triboroxine pyridine complex (5.0 g, 20.8 mmol) and $K_2CO_3$ (8.5 g, 62.0 mmol). The reaction mixture is stirred and $N_2$ is bubbled in for 15 min. Tetrakis(triphenylphosphine) palladium(0) (1.8 g, 1.6 mmol) is added at room temperature and $N_2$ is bubbled in for additional 20 min. The reaction mixture is heated to 80° C. and stirred for 18 hours, when the GC-MS showed the reaction is complete. The mixture is filtered and washed with ether (400 mL) and water (50 mL). The organic layer is separated and washed with brine and dried over $MgSO_4$. The solvents were removed and the residue is purified through a flash chromatographic column with a gradient of hexanes/ether to give 2,4-dichloro-3-vinylaniline.

To a solution of 2,4-dichloro-3-vinylaniline (4.9 g, 26 mmol) in EtOAc (60 mL) is added 10% Pd/C (0.50 g). The pressure flask is filled with $H_2$ at 55 psi and shaken for 2 hrs. Excess $H_2$ is removed and the mixture is filtered through a pad of celite. The solvent is removed and the resulting mixture is purified through a flash chromatographic column with a gradient of hexanes/ether to give 2,4-dichloro-3-ethylaniline.

C. 2-Fluoro-4-methyl-3-trifluoroaniline

To a solution of 2-fluoro-3-trifluoromethylaniline (5.0 g, 28 mmol) in DMF (25 mL) is added a solution of NBS (5.0 g, 28 mmol) in DMF (25 mL). After 2.5 h, the reaction is partitioned between ether and saturated aqueous NaCl. The separated organic phase is washed twice with fresh saturated aqueous NaCl, dried over $Na_2SO_4$, and concentrated under reduced pressure to give 4-bromo-2-fluoro-3-trifluoromethylaniline as an oil.

The bromide above (10.0 g, 38.8 mmol), trimethylboroxine (4.9 g, 38.8 mmol), $K_2CO_3$ (16.1 g, 116 mmol), and palladium tetrakistriphenylphosphine (4.5 g, 3.9 mmol) are heated under a nitrogen atmosphere. A second aliquot of trimethylboroxine (4.9 g, 38.8 mmol) is added to consume the starting bromide. After 18 h, the cooled reaction is partitioned between EtOAc and saturated aqueous NaCl. The separated organic layer is washed with fresh brine (3×), dried with $Na_2SO_4$, and concentrated under reduced pressure. The residue is purified by flash chromatography ($Et_2O$/hexanes) to give the title aniline.

D. 2-Fluoro-4-ethyl-3-trifluoroaniline

4-Bromo-2-fluoro-3-trifluoromethylaniline described above (5.0 g, 19.4 mmol) and tributylvinyltin chloride (7.1 g, 20.4 mmol) are added to anhydrous DMF (100 mL). The solution is degassed with $N_2$, palladium tetrakistriphenylphosphine (1.5 g, 1.3 mmol) is added, and the reaction is heated at 120° C. for 18 hours. After cooling, the reaction mixture is partitioned between $Et_2O$ and saturated aqueous NaCl. The separated ether layer is washed with fresh saturated aqueous NaCl (2×), dried with $Na_2SO_4$, and concentrated under reduced pressure. The residue is purified by flash chromatography eluting with 5, then 10, then 20% EtOAc in hexanes to give the desired product, 2-fluoro-3-trifluoromethyl-4-vinylaniline.

2-Fluoro-3-trifluoromethyl-4-vinylaniline prepared above (4.0 g, 19.4 mmol) is dissolved in EtOH and degassed with $N_2$, and 10% Pd on charcoal (0.5 g) is added. The mixture is placed in a Parr apparatus and treated with $H_2$ at room temperature. The reaction is flushed with $N_2$ and filtered. The filter pad is washed with fresh EtOH and the filtrates are combined. Concentrated HCl (6.5 mL) is added to the cooled filtrate (0° C.) before removal of the volatiles under reduced pressure. The resulting white solid is washed with $Et_2O$ and collected by filtration to give 4-ethyl-2-fluoro-3-trifluoromethylaniline hydrochloride.

The free aniline is prepared from the hydrochloride salt by partitioning between $Et_2O$ and a saturated aqueous $NaHCO_3$ solution. The separated organic layer is washed with brine, dried ($Na_2SO_4$) and concentrated in vacuo to give 4-ethyl-2-fluoro-3-trifluoromethylaniline as an oil.

E. 4-Chloro-2-fluoro-3-methylaniline

To 6-chloro-2-fluoro-3-methylbenzoic acid (10 g, 53 mmol) is added $CH_2Cl_2$ (60 mL), DMF (0.5 mL) and oxalyl chloride (9.25 mL, 106 mmol). The reaction mixture is allowed to stir until it reaches homogeneity and is then concentrated in vacuo. The residue is poured onto a 50:50 mixture of ice and 36% ammonium hydroxide to yield 6-chloro-2-fluoro-3-methylbenzamide.

The 6-chloro-2-fluoro-3-methylbenzamide prepared above is dissolved in MeOH. Sodium methoxide (16.1 g, 298 mmol) is added and the reaction is heated to reflux. NBS (21.2 g, 119 mmol) is then added portionwise as a solid and the reaction mixture is stirred at reflux an additional 2 hours. After cooling, volatiles are removed under reduced pressure and the residue is diluted with EtOAc and water. The organic phase is separated and the water layer is extracted with fresh EtOAc (3×). The combined organic layers are dried ($MgSO_4$), filtered and concentrated in vacuo to give N-6-chloro-2-fluoro-3-methyl-phenyl)carbamic acid methyl ester.

The carbamate prepared above is dissolved in MeOH (220 mL) and water (22 mL). Potassium hydroxide (31 g, 560 mmol) is added and the reaction heated at reflux for 12 hours. After cooling the reaction to room temperature, the MeOH is removed under reduced pressure and the residue is diluted with water and extracted with $CH_2Cl_2$ (3×). The combined organic layers are dried ($MgSO_4$), filtered and concentrated in vacuo. The residue is purified by flash chromatography using 10% EtOAc in hexane to give 6-chloro-2-fluoro-3-methylaniline.

To 6-chloro-2-fluoro-3-methylbenzoic acid (10 g, 53 mmol) is added $CH_2Cl_2$ (60 mL), DMF (0.5 mL) and oxalyl chloride (9.25 mL, 106 mmol). The reaction mixture is allowed to stir until it reaches homogeneity and is then concentrated in vacuo. The residue is poured onto a 50:50 mixture of ice: 36% ammonium hydroxide to yield 6-chloro-2-fluoro-3-methylbenzamide.

The 6-chloro-2-fluoro-3-methylbenzamide prepared above is dissolved in MeOH. Sodium methoxide (16.1 g, 298 mmol) is added and the reaction is heated to reflux. NBS (21.2 g, 119 mmol) is then added portionwise as a solid and the reaction mixture is stirred at reflux an additional 2 hours. After cooling, volatiles are removed under reduced pressure and the residue is diluted with EtOAc and water. The organic phase is separated and the water layer is extracted with fresh EtOAc (3×). The combined organic layers are dried ($MgSO_4$), filtered and concentrated in vacuo to give N-6-chloro-2-fluoro-3-methyl-phenyl)carbamic acid methyl ester.

The carbamate prepared above is dissolved in MeOH (220 mL) and water (22 mL). Potassium hydroxide (31 g, 560 mmol) is added and the reaction heated at reflux for 12 hours. After cooling the reaction to room temperature, the MeOH is removed under reduced pressure and the residue is diluted with water and extracted with $CH_2Cl_2$ (3×). The combined organic layers are dried ($MgSO_4$), filtered and concentrated in vacuo. The residue is purified by flash chromatography using 10% EtOAc in hexane to give 6-chloro-2-fluoro-3-methylaniline.

F. 4-Chloro-2-fluoro-3-ethylaniline

To a solution of 4-chloro-2-fluoroaniline (50.0 g, 344 mmol) in AcOH (30 mL) is added $Ac_2O$ (60 mL) and the reaction is stirred at room temperature for 2 hours. The mixture is poured into ice water (500 mL) to give a solid precipitate. The mixture is stirred for an additional 1 hour at room temperature. The solid is filtered and washed with water and hexanes, then air dried to give N-(4-chloro-2-fluorophenyl)acetamide.

To a solution of N-(4-chloro-2-fluorophenyl)acetamide (10.0 g, 53.3 mmol) and diisopropylamine (7.5 mL, 53.3 mmol) in THF (300 mL) at −78° C. is added dropwise n-BuLi (2.5 M in hexanes, 42.6 mL, 106.6 mmol) keeping the reaction temperature below −60° C. After 2 hours, iodoethane (12.4 g, 80 mmol) is added dropwise at −78° C. The reaction mixture is stirred at −78° C. for additional 1.5 hours. A 1N solution of aqueous HCl is added slowly until a pH between 4 and 5 is reached. The mixture is extracted with EtOAc (200 mL×3) and the organic layers are combined washed with water and brine, then dried over $MgSO_4$. The solvent is removed under reduced pressure and the solid residue is stirred in ether and hexane (1:4, 80 mL) for 1 hour. The filtered solid is dried to give N-(4-chloro-3-ethyl-2-fluorophenyl)acetamide.

To a solution of N-(4-chloro-3-ethyl-2-fluorophenyl)acetamide (11.0 g, 51.0 mmol) in MeOH (80 mL) is added concentrated HCl (40 mL) before heating at reflux for 16 hours. The solvent is removed from the cooled reaction under reduced pressure maintaining the water bath below 45° C. The residue is cooled with an ice bath before a 3N NaOH solution is added to adjust pH between 9 and 10. The mixture is extracted with ether and dried over $MgSO_4$. The solvent is removed and the residue is purified through a flash chromatography using a gradient of ether/hexanes to give 4-chloro-3-ethyl-2-fluoroaniline.

Similarly prepared is:
4-chloro-3-methyl-2-fluoroaniline.

G. 4-Chloro-2-fluoro-3-isopropylaniline

To a solution of N-(4-chloro-2-fluorophenyl)acetamide prepared above (12.0 g, 64 mmol) in THF (300 mL) at −78° C. is added dropwise n-BuLi (2.0 M in cyclohexane, 64 mL, 128 mmol) keeping the reaction temperature below −60° C. The reaction mixture is stirred between −60 to −70° C. for 2 hours and 1,1,1-trifluoro-2-iodoethane (20.1 g, 96 mmol) is added dropwise at −78° C. The mixture is stirred at this temperature for additional 3 hrs. Then a 1N HCl (200 mL) solution is added slowly at −78° C. The mixture is allowed to warm to room temperature and extracted with EtOAc (200 mL×3). The combined organic layers are washed with water and brine, then dried over $MgSO_4$. The solvent is removed and the residue is stirred in ether and hexanes (1:2, 120 mL) for 1 hour. The solid is filtered to give N-(4-chloro-2-fluoro-3-iodophenyl)acetamide.

To a mixture of N-(4-chloro-2-fluoro-3-iodophenyl)acetamide (20.0 g, 64 mmol) in MeOH (80 mL) is added concentrated HCl (60 mL). The mixture is stirred at reflux for 18 hours before cooling to room temperature and removal of the solvent under reduced pressure while maintaining the water bath below 45° C. The residue is cooled with an ice bath and a 1N NaOH solution is added to adjust the pH between 9 and 10. The aqueous phase is extracted with ether and dried over $MgSO_4$. The solvent is removed and the residue is purified through a flash chromatographic column with a gradient of hexanes/ether to give 4-chloro-2-fluoro-3-iodoaniline.

To a solution of 4-chloro-2-fluoro-3-iodoaniline (13.5 g, 50 mmol) in DME/water (150 mL/50 mL) is added 2-propeneboronic acid (6.4 g, 74.6 mmol) and $K_2CO_3$ (20.6 g, 150 mmol). Nitrogen gas is bubbled in for 15 min before tetrakis(triphenylphosphine)palladium(0) (2.8 g, 2.5 mmol) is added at room temperature. Nitrogen is bubbled in for additional 20 minutes before the reaction mixture is heated to 80° C. for 18 hours. The mixture is filtered through a pad of celite and washed with ether (400 mL) and water (50 mL). The organic layer is separated and washed with brine and dried over $MgSO_4$. The solvent is removed and the residue is purified through a flash chromatographic column with a gradient of hexanes/ether to give 4-chloro-3-isopropene-2-fluoroaniline.

To a solution of 4-chloro-3-isopropene-2-fluoroaniline (4.5 g, 24.2 mmol) in EtOAc (50 mL) is added 10% Pt/C (0.45 g). The pressure flask is filled with H$_2$ at 50 psi and shaken at room temperature for 4 hrs. The excess H$_2$ is removed and the mixture is filtered through a pad of celite. The solvent is removed and the resulting mixture is purified through a flash chromatographic column with a gradient of hexanes/ether to give 4-chloro-3-isopropane-2-fluoroaniline.

Example 2

2-Iodophenylacetic Acid Ester and Phenylacetamide Starting Materials

Prepared according to, e.g., *J Med Chem*, Vol. 33, pp. 2358-2368 (1990), U.S. Pat. No. 6,291,523 and International Application WO 99/11605, starting from the corresponding benzoic acid or 2-indolinone, are, for instance:
N,N-dimethyl-5-methyl-2-iodophenylacetamide;
N,N-dimethyl-5-ethyl-2-iodophenylacetamide;

Example 3

5-Ethyl-2-(2'-fluoro-4'-methyl-3'-trifluoromethylanilino)phenylacetic acid N,N-dimethyl amide A mixture of N,N-dimethyl-5-ethyl-2-iodophenylacetamide (2.0 g, 6.3 mmol), 2-fluoro-methyl-3-trifluoromethylaniline (2.4 g, 12.6 mmol), copper (0.2 g, 3.2 mmol), cuprous iodide (0.6 g, 3.2 mmol), and K$_2$CO$_3$ (0.9 g, 6.3 mmol) in xylenes (6.0 mL) are heated at reflux for 24 h. After cooling, the crude reaction mixture is diluted with EtOAc and filtered through Celite®. The filtrate is concentrated under reduced pressure. The residue is purified by flash chromatography, eluting with hexanes, then up to 25% EtOAc/hexane mixtures to give the target compound 5-ethyl-2-(2'-fluoro-4'-methyl-3'-trifluoromethylanilino)phenylacetic acid N,N-dimethyl amide.

Similarly prepared are:
5-Methyl-2-(2'-fluoro-4'-methyl-3'-trifluoromethylanilino) phenylacetic acid N,N-dimethyl amide.
5-Methyl-2-(2'-fluoro-4'-bromo-3'-trifluoromethylanilino) phenylacetic acid N,N-dimethyl amide.
5-Methyl-2-(2',4'-dichloro-3'-methylanilino)phenylacetic acid N,N-dimethyl amide.
5-Ethyl-2-(2',4'-dichloro-3'-methylanilino)phenylacetic acid N,N-dimethyl amide.
5-Methyl-2-(2',4'-dichloro-3'-ethylanilino)phenylacetic acid N,N-dimethyl amide.
5-Ethyl-2-(2',4'-dichloro-3'-ethylanilino)phenylacetic acid N,N-dimethyl amide.
5-Methyl-2-(2'-fluoro-4'-chloro-3'-methylanilino)phenylacetic acid N,N-dimethyl amide.
5-Ethyl-2-(2'-fluoro-4'-chloro-3'-methylanilino)phenylacetic acid N,N-dimethyl amide.
5-Methyl-2-(2'-fluoro-4'-chloro-3'-ethylanilino)phenylacetic acid N,N-dimethyl amide.
5-Ethyl-2-(2'-fluoro-4'-chloro-3'-ethylanilino)phenylacetic acid N,N-dimethyl amide.
5-Ethyl-2-(2'-fluoro-4'-chloro-3'-isopropylanilino)phenylacetic acid N,N-dimethyl amide.

Example 4

5-Methyl-2-(2'-fluoro-4'-ethyl-3'-trifluoromethylanilino)phenylacetic acid N,N-dimethyl amide 5-Methyl-2-(2'-fluoro-4'-bromo-3'-trifluoromethylanilino)phenylacetic acid N,N-dimethyl amide prepared by method outlined in example 3 (0.8 g, 1.7 mmol), Pd(PPh$_3$)$_4$ (0.1 g, 0.09 mmol), and vinyl tributylstannane (0.6 g, 1.9 mmol) in DMF (5 mL) is heated to 120° C. under nitrogen overnight. After cooling, the reaction is portioned between EtOAc and saturated aqueous solution of NaCl. The separated organic layer is washed twice with fresh saturated aqueous solution of NaCl. The EtOAc layer is dried and concentrated under reduced pressure. The residue is purified by flash chromatography to give 5-Methyl-2-(2'-fluoro-4'-vinyl-3'-trifluoromethylanilino)phenylacetic acid N,N-dimethyl amide.

The above styrene is reduced under conditions outlined in. The styrene is dissolved in i-PrOH and toluene and degassed for 10 minutes. Then Cs$_2$CO$_3$ (22 mg, 0.07 mmol), [Ir(cod) Cl]$_2$ (44 mg, 0.07 mmol), and dppp (27 mg, 0.07 mmol) are added and the reaction is heated to 80° C. over night. The cooled solution is concentrated in vacuo and the residue purified by flash chromatography eluting with 10, then 20, then 30% EtOAc/hexanes to give the title 5-methyl-2-(2'-fluoro-4'-ethyl-3'-trifluoromethylanilino)phenylacetic acid N,N-dimethyl amide.

Example 5

5a) 5-Ethyl-2-(2'-fluoro-4'-methyl-3'-trifluoromethylanilino)phenylacetic acid

A solution of the above 5-ethyl-2-(2'-fluoro-4'-methyl-3'-trifluoromethylanilino)phenylacetic acid N,N-dimethyl amide described in Example 3 (0.9 g, 2.4 mmol) in EtOH (25 mL) and 4N NaOH (12 mL) is heated to 80° C. overnight. After cooling, the reaction is concentrated under reduced pressure and diluted with ice cold EtOAc. The pH of the aqueous layer is adjusted to 1-2 with ice cold 2.5 N HCl. The separated organic layer is dried with Na$_2$SO$_4$ and concentrated to a solid. The solid is purified by trituration with an Et$_2$O/hexane mixture to give the title acid, 5-ethyl-2-(2'-fluoro-4'-methyl-3'-trifluoromethylanilino)phenylacetic acid.

MS m/z 356 (ES$^+$), 354 (ES$^-$)
CHN found C, 60.47; H, 4.47; N, 3.73.
Similarly prepared are:

5b) 5-Methyl-2-(2'-fluoro-4'-methyl-3'-trifluoromethylanilino)phenylacetic acid

MS m/z 342 (ES$^+$), 340 (ES$^-$)
CHN found C, 59.56; H, 4.36; N, 3.91.

5c) 5-Methyl-2-(2'-fluoro-4'-ethyl-3'-trifluoromethylanilino)phenylacetic acid $^1$H NMR (400 MHz, DMSO-d$_6$) δ ppm 1.13 (t, J=7.3 Hz, 3H), 2.27 (s, 3H), 2.63-2.70 (m, 2H), 3.56 (s, 2H), 6.87 (t, J=8.6 Hz, 1H), 7.02-7.09 (m, 2H), 7.12 (s, 1H), 7.43 (s, 1H).
MS m/z 356 (ES$^+$), 354 (ES$^-$)

5d) 5-Ethyl-2-(2'-fluoro-4'-ethyl-3'-trifluoromethylanilino)phenylacetic acid $^1$H NMR (400 MHz, DMSO-d$_6$) δ ppm 1.17 (t, J=7.5 Hz, 3H), 1.26 (t, J=7.5 Hz, 3H), 2.59 (q, J=7.5 Hz, 2H), 2.89 (q, J=7.1 Hz, 2H), 3.75 (d, J=22.7 Hz 1H), 3.83 (d, J=22.7 Hz, 1H), 6.52 (d, J=8.1 Hz, 1H), 7.06 (d, J=8.1 Hz, 1H), 7.23 (s, 1H), 7.50 (d, J=8.3 Hz, 1H), 7.79 (t, J=7.8 Hz, 1H).
MS m/z 370 (ES$^+$), 368 (ES$^-$)

5e) 5-Methyl-2-(2',4'-dichloro-3'-methylanilino)phenylacetic acid $^1$H NMR (400 MHz, DMSO-d$_6$) δ ppm 2.29 (s, 3H), 2.41 (s, 3H), 3.51 (s, 2H), 6.51 (d, J=8.8 Hz, 1H), 7.07-7.22 (m, 4H), 12.46 (s, 1H)
MS m/z 324, 326, 328 (ES$^+$), 322, 324, 326 (ES$^-$)

5f) 5-Ethyl-2-(2',4'-dichloro-3'-methylanilino)phenylacetic acid

MS m/z 338, 340, 342 (ES$^+$), 336, 338, 340 (ES$^-$)
CHN found C, 59.97; H, 4.71; N, 4.12.

5g) 5-Methyl-2-(2',4'-dichloro-3'-ethylanilino)phenylacetic acid $^1$H NMR (400 MHz, DMSO-d$_6$) δ ppm 1.14 (t, J=7.5 Hz, 3H), 2.29 (s, 3H), 2.88 (q, J=7.5 Hz, 2H), 3.52 (s, 2H), 6.52 (d, J=9.0 Hz, 1H), 7.07-7.18 (m, 4H), 7.25 (s, 1H), 12.49 (br. s., 1H)
CHN found C, 60.53; H, 5.19; N, 3.98.

5h) 5-Ethyl-2-(2',4'-dichloro-3'-ethylanilino)phenylacetic acid $^1$H NMR (400 MHz, DMSO-d$_6$) δ ppm 1.11-1.22 (m, 6H), 2.52-2.63 (m, 4H), 2.88 (q, J=7.5 Hz, 2H), 3.54 (s, 2H), 6.55 (d, J=9.0 Hz, 1H), 7.11-7.15 (m, 3H), 7.18 (s, 1H), 7.26 (s, 1H), 12.50 (br. s., 1H)
CHN found C, 61.39; H, 5.22; N, 4.24.

5i) 5-Methyl-2-(2'-fluoro-4'-chloro-3'-methylanilino)phenylacetic acid

MS m/z 308 (ES$^+$), 306 (ES$^-$)
CHN found C, 62.16; H, 4.79; N, 4.49.

5j) 5-Ethyl-2-(2'-fluoro-4'-chloro-3'-methylanilino)phenylacetic acid

MS m/z 322 (ES$^+$), 320 (ES$^-$)
CHN found C, 63.20; H, 5.22; N, 4.32.

5k) 5-Methyl-2-(2'-fluoro-4'-chloro-3'-ethylanilino)phenylacetic acid $^1$H NMR (400 MHz, DMSO-d$_6$) δ ppm 1.15 (t, J=7.5 Hz, 3H), 2.27 (s, 3H), 2.72 (qd, J=7.5, 2.1 Hz, 2H), 3.54 (s, 2H), 6.55 (t, J=9.0 Hz, 1H), 6.98-7.07 (m, 3H), 7.10 (s, 1H), 7.30 (br. s., 1H), 12.35 (br. s., 1H)
MS m/z 322 (ES$^+$), 320 (ES$^-$)
CHN found C, 63.54; H, 5.28; N, 4.38.

5l) 5-Ethyl-2-(2'-fluoro-4'-chloro-3'-ethylanilino)phenylacetic acid $^1$H NMR (400 MHz, DMSO-d$_6$) δ ppm 1.12-1.20 (m, 6H), 2.57 (q, J=7.7 Hz, 2H), 2.68-2.76 (m, 2H), 3.56 (s, 2H), 6.58 (t, J=9.0 Hz, 1H), 7.00 (dd, J=9.0, 1.5 Hz, 1H), 7.04-7.10 (m, 2H), 7.13 (s, 1H), 7.31 (s, 1H), 12.36 (s, 1H)
CHN found C, 64.20; H, 5.61; N, 4.37.

5m) 5-Ethyl-2-(2'-fluoro-4'-chloro-3'-isopropylanilino)phenylacetic acid $^1$H NMR (400 MHz, CDCl$_3$) δ ppm 1.23 (t, J=7.7 Hz, 3H), 1.37 (dd, J=7.0, 1.3 Hz, 6H), 2.62 (q, J=7.7 Hz, 2H), 3.46-3.60 (m, 1H), 3.68 (s, 2H), 6.72 (t, J=8.8 Hz, 1H), 6.92 (dd, J=8.8, 1.8 Hz, 1H), 7.07-7.14 (m, 2H), 7.23 (d, J=8.1 Hz, 1H)
CHN found C, 65.08; H, 6.16; N, 3.84.

Example 6

6a) 5-Methyl-2-(2',4'-dichloro-3'-methylanilino)phenylacetic acid diethylamine salt A suspension of 600 mg 5-Methyl-2-(2',4'-dichloro-3'-methylanilino)phenylacetic acid (1.85 mmoles) in 6 ml tert. Butyl methyl ether (TBME) is heated to 40° C. 137 mg diethylamine (1.85 mmoles) are dropwise added. The resulting slightly cloudy solution is clarified via hot filtration through a Whatman glasfiber filter. The filter is rinsed with 2 ml TBME of 40° C. The filtrate is allowed to cool slowly.

The solution is seeded at 30° C. and crystallization takes place. The suspension is stirred for ca. 15 h at room temperature and then for 2 h at 0° C. The slurry is filtered and the filter cake washed with 4.5 ml TBME of 0° C. The crystals are dried for 4 h at 50° C. and ca. 10 mbar to yield a white powder, m.p. 115-116° C.

6b) sodium 5-Methyl-2-(2',4'-dichloro-3'-methylanilino)phenylacetate

A suspension of 400 mg 5-Methyl-2-(2',4'-dichloro-3'-methylanilino)phenylacetic acid (1.23 mmoles) in 4 ml acetone is heated to 50° C. The resulting almost clear solution is clarified via hot filtration through a Whatman glasfiber filter. The filter is rinsed with 2 ml acetone of 50° C. 165 mg 30% aqueous natriumhydroxide solution (1.23 mmoles) are added at 50° C. The solution is allowed to cool to room temp. and seeded at ca. 25° C. Crystallization takes then very slowly place. The suspension is stirred for ca. 15 h at room temperature and then for 2 h at 0° C. After filtration only 97 mg wet crystals are obtained. The crystals and the mother liquor are combined and 6 ml isopropylacetate are added dropwise under stirring. The thick suspension is filtered and the solid washed with isopropylacetate. The salt is dried first for 2 h at 50° C./ca. 10 mbar and then for 16 h at 80° C. and ca. 10 mbar to yield the salt as a white powder, m.p. 254-255° C.
Water assay: 2.31% m/m

6c) 5-Methyl-2-(2',4'-dichloro-3'-methylanilino)phenylacetic acid tromethamine salt A suspension of 1.30 g 5-Methyl-2-(2',4'-dichloro-3'-methylanilino)phenylacetic acid (4.01 mmoles) in 13 ml acetone is heated to 55° C.

The resulting almost clear solution is clarified via hot filtration through a Whatman glasfiber filter. The filter is rinsed with 2.6 ml acetone of 50° C. A solution of 0.487 g tromethamine (Trisma base) (4.01 mmoles) in 1 ml water is added dropwise at 50° C. The dropping funnel is rinsed with 0.5 ml water. The solution is allowed to cool to room temp. and seeded at ca. 40° C. Crystallization takes then place. The suspension is stirred for ca. 15 h at room temperature and then for 2 h at 0° C. The slurry is filtered and the solid washed with 6 ml acetone. The salt is dried first for 2 h at 50° C./ca. 10 mbar and then for 16 h at 80° C. and ca. 10 mbar to yield the salt as a white powder, m.p. 156-157° C., DSC 162.0° C., melting enthalpy 132 J/g.

Principal X-Ray Diffraction Peaks:

| Angle 2-Theta ° | d value Angstrom | Intensity Count | Intensity % |
|---|---|---|---|
| 4.371 | 20.19907 | 360 | 66.7 |
| 13.276 | 6.66382 | 525 | 97.2 |
| 13.719 | 6.44934 | 312 | 57.8 |
| 14.443 | 6.12802 | 316 | 58.5 |
| 14.943 | 5.9239 | 356 | 65.9 |
| 15.663 | 5.65321 | 318 | 58.9 |
| 16.948 | 5.22734 | 403 | 74.6 |
| 17.739 | 4.99598 | 304 | 56.3 |
| 22.832 | 3.89177 | 464 | 85.9 |
| 23.707 | 3.75003 | 389 | 72 |
| 24.877 | 3.57629 | 323 | 59.8 |
| 25.868 | 3.44143 | 217 | 40.2 |
| 26.596 | 3.34886 | 540 | 100 |

6d) calcium 5-Methyl-2-(2',4'-dichloro-3'-methylanilino)phenylacetate monohydrate A suspension of 1.30 g 5-Methyl-2-(2',4'-dichloro-3'-methylanilino)phenylacetic acid (4.01 mmoles) in 13 ml acetone is heated to 55° C. 0.535 g 30% aqueous sodium hydroxide solution (4.01 mmoles) are added. The resulting almost clear solution is clarified via filtration at 50° C. through a Whatman glasfiber filter. The filter is rinsed with 3.9 ml acetone of 50° C. Then a solution of 0.51 g calciumchloride (4.41 mmoles) in 1 ml water is added dropwise at 50° C. The dropping funnel is rinsed with 0.5 ml water. The resulting thick suspension is allowed to cool to room temperature. Further 7 ml water are added at 25° C. The mixture is stirred at r.t. for 1 h and filtered. The filter cake is washed with 20 ml acetone/water 2:1 v/v and then with 5 ml acetone. the crystallisate is dried for 2 h at 50° C./ca. 10 mbar and then for 16 h at 80° C. and ca. 10 mbar. As the salt is still contaminated with some natriumchloride the crystals are suspended in 13.5 ml water and 1.5 ml acetone and the suspension stirred for 1 h at r.t. After filtration the filter cake is washed with 8 ml water/acetone 9:1 v/v in 4 portions. The salt is dried first for 2 h at 50° C./ca. 10 mbar and then for 16 h at 80° C. and ca. 10 mbar to yield a white powder, m.p. 278-279° C., DSC 147.1/224.2° C., melting enthalpy 121/2 J/g.

Water assay: 2.63% m/m

Principal X-Ray Diffraction Peaks:

| Angle 2-Theta ° | d value Angstrom | Intensity % |
|---|---|---|
| 6.273 | 14.07919 | 100 |
| 10.622 | 8.32204 | 30.7 |
| 11.106 | 7.96028 | 34.8 |
| 13.38 | 6.61206 | 33.7 |
| 14.348 | 6.16798 | 25.5 |
| 16.473 | 5.37693 | 48.2 |
| 18.634 | 4.75806 | 29.2 |
| 21.394 | 4.15001 | 34.7 |
| 23.887 | 3.72226 | 27.8 |
| 24.498 | 3.63067 | 23.5 |
| 25.395 | 3.5045 | 19 |

6e) Lysine 5-Methyl-2-(2',4'-dichloro-3'-methylanilino)phenylacetate monohydrate A suspension of 400 mg 5-Methyl-2-(2',4'-dichloro-3'-methylanilino)phenylacetic acid (1.23 mmoles) in 4 ml acetone is heated to 50° C. The resulting almost clear solution is clarified via hot filtration through a Whatman glasfiber filter. The filter is rinsed with 4 ml acetone of 50° C. A solution of 184 mg lysine (1.23 mmoles) in 1 ml water is added dropwise. The resulting thick suspension is kept for 30 min. at 50° C. and then allowed to cool to room temperature. The mixture is further stirred at ca. 25° C. over night and filtered. The filter cake is washed with 6 ml acetone. The crystals are dried first for 2 h at 50° C./ca. 10 mbar and then for 16 h at 80° C. and ca. 10 mbar to yield a white powder, m.p. 162-163° C.

Water assay: 3.80% m/m

6f) choline 5-Methyl-2-(2',4'-dichloro-3'-methylanilino)phenylacetate monohydrate A suspension of 400 mg 5-Methyl-2-(2',4'-dichloro-3'-methylanilino)phenylacetic acid (1.23 mmoles) in 4 ml acetone is heated to 50° C. 305 mg choline solution 50% in water (1.23 mmoles) are added. The resulting almost clear solution is clarified via hot filtration through a Whatman glasfiber filter. The filter is rinsed with 2 ml acetone of 50° C. 6 ml tert. Butyl methyl ether (TBME) are slowly added at 40° C. to the filtrate. The slightly cloudy solution is allowed to cool and seeded at 25° C. Crystallization takes then very slowly place. The mixture is stirred over night at r.t. After 16 h, 12 ml additional TBME are added dropwise. The thick suspension is stirred further for 2 h at 25° C. and filtered.

The solid is washed with 6 ml TBME/acetone 9/1 v/v and dried for 4 h at 50° C. and ca 10 mbar to yield a white powder, m.p. 105-106° C.

Water assay: 4.55% m/m

6g) Potassium 5-Methyl-2-(2',4'-dichloro-3'-methylanilino)phenylacetate

A suspension of 5-Methyl-2-(2',4'-dichloro-3'-methylanilino)phenylacetic acid (15.42 mmoles) in acetone is heated to reflux temperature and allow to stir for 10 min at ca. 55° C. The resulting solution is slightly cooled to 50° C. and filtered hot over Whatman glasfiber filter. The filter is washed with acetone at 50° C. The filtrate is heated to 50° C. and a mixture of potassium hydroxide 45% (14.65 mmoles) (0.95 eq.) and water is dropwise added over ca. 15 min. The dropping funnel is rinsed with water and acetone. The resulting suspension is stirred at 50° C. for 30 min. The slurry is then allowed to cool to 25° C. over ca. 2 hours. The suspension is stirred over night at room temperature and filtered. The filter cake is washed in three portions. The crystals are dried first for 3 h at 50° C./10 mbar and then further for 17 h at 80° C./10 mbar to yield a white powder, m.p. 315-317° C., 326.9° C., melting enthalpy 29 J/g.

Principal X-Ray Diffraction Peaks:

| Angle 2-Theta ° | d value Angstrom | Intensity % |
|---|---|---|
| 6.263 | 14.10146 | 100 |
| 10.932 | 8.08664 | 38.2 |
| 12.602 | 7.01831 | 24.7 |
| 13.614 | 6.49915 | 25.2 |
| 14.689 | 6.02592 | 22.6 |

-continued

| Angle 2-Theta ° | d value Angstrom | Intensity % |
|---|---|---|
| 16.669 | 5.31402 | 26.9 |
| 18.904 | 4.69055 | 31.7 |
| 21.442 | 4.14078 | 14.9 |
| 21.958 | 4.04458 | 17.3 |
| 22.829 | 3.89219 | 15.7 |
| 24.24 | 3.66874 | 22.6 |
| 26.114 | 3.40963 | 25.8 |
| 26.698 | 3.33632 | 36.4 |
| 26.988 | 3.30112 | 19.8 |
| 28.026 | 3.1812 | 33.1 |
| 29.173 | 3.05867 | 13.8 |

The invention claimed is:

1. A method of treating rheumatoid arthritis, osteoarthritis, dysmenorrhea, pain or inflammation in mammals which comprises administering to a mammal in need thereof a correspondingly effective amount of a compound selected from the group consisting of 5-methyl-2-(2',4'-dichloro-3'-methylanilino)phenylacetic acid;

5-Methyl-2-(2',4'-dichloro-3'-methylanilino)phenylacetic acid diethylamine salt;

sodium 5-Methyl-2-(2',4'-dichloro-3'-methylanilino)phenylacetate;

5-Methyl-2-(2',4'-dichloro-3'-methylanilino)phenylacetic acid tromethamine salt;

calcium 5-Methyl-2-(2',4'-dichloro-3'-methylanilino)phenylacetate monohydrate;

Lysine 5-Methyl-2-(2',4'-dichloro-3'-methylanilino)phenylacetate monohydrate; and choline 5-Methyl-2-(2',4'-dichloro-3'-methylanilino)phenylacetate monohydrate.

* * * * *